United States Patent
Huber et al.

(10) Patent No.: US 11,262,185 B2
(45) Date of Patent: Mar. 1, 2022

(54) METHOD FOR MONITORING TIME-DEPENDENT PROPERTIES OF LIGHT DURING SCANNING SWEPT-SOURCE OPTICAL COHERENCE TOMOGRAPHY

(71) Applicant: OPTORES GMBH, Munich (DE)

(72) Inventors: Robert Huber, Lübeck (DE); Wolfgang Draxinger, Lübeck (DE); Tom Pfeiffer, Lübeck (DE)

(73) Assignee: OPTORES GMBH, Munich (DE)

( * ) Notice: Subject to any disclaimer, the term of this patent is extended or adjusted under 35 U.S.C. 154(b) by 0 days.

(21) Appl. No.: 17/260,643

(22) PCT Filed: Jul. 19, 2019

(86) PCT No.: PCT/EP2019/069473
§ 371 (c)(1),
(2) Date: Jan. 15, 2021

(87) PCT Pub. No.: WO2020/016399
PCT Pub. Date: Jan. 23, 2020

(65) Prior Publication Data
US 2021/0247174 A1 Aug. 12, 2021

(30) Foreign Application Priority Data
Jul. 19, 2018 (DE) .......................... 102018212100.1

(51) Int. Cl.
*G01B 9/02* (2006.01)
*A61B 3/10* (2006.01)
(Continued)

(52) U.S. Cl.
CPC ............ *G01B 9/02091* (2013.01); *A61B 3/10* (2013.01); *A61B 5/7203* (2013.01);
(Continued)

(58) Field of Classification Search
CPC ............ G01B 9/02091; G01B 9/02041; G01B 9/02083; G01B 9/02069; G01B 9/02004;
(Continued)

(56) References Cited

U.S. PATENT DOCUMENTS

| | | | |
|---|---|---|---|
| 2014/0028997 A1* | 1/2014 | Cable | A61B 5/0066 356/51 |
| 2015/0109621 A1* | 4/2015 | Huber | G01B 9/0203 356/479 |

(Continued)

FOREIGN PATENT DOCUMENTS

| | | |
|---|---|---|
| DE | 102009022958 | 12/2010 |
| DE | 102018212100 | 1/2020 |

(Continued)

OTHER PUBLICATIONS

Kolb et al. "1060nm FDML laser with centimeter coherence length and 1.67 MHz sweep rate for full eye length and retinal ultra-widefield OCT," Proceedings of SPIE-OSA, Aug. 2017, vol. 10416, 104160J, 8 pages.

(Continued)

*Primary Examiner* — Dominic J Bologna
(74) *Attorney, Agent, or Firm* — Sheridan Ross P.C.

(57) ABSTRACT

A method comprises: splitting laser light into sample light, reference light, and monitor light; routing the reference light into a reference arm of an OCT interferometer; routing the monitor light into a monitor device, which generates at least one optical monitor signal representing at least one time-dependent property of the monitor light; generating at least one electric monitor signal from the at least one optical monitor signal; illuminating in a point-shaped manner a sample with sample light, wherein the illumination point is guided on the surface of the sample along a predetermined trajectory; superimposing the light scattered by the sample with the reference light emerging from the reference arm to (Continued)

generate an electric OCT signal; wherein the at least one electric monitor signal and the electric OCT signal are AD-converted in alternating sequence, in each case equidistantly in time, to form a single digital data stream.

10 Claims, 2 Drawing Sheets

(51) Int. Cl.
    *A61B 5/00*     (2006.01)
    *G01B 9/02091*  (2022.01)
    *G01B 9/02004*  (2022.01)
    *G01B 9/02055*  (2022.01)

(52) U.S. Cl.
    CPC ........ *A61B 5/7257* (2013.01); *G01B 9/02004* (2013.01); *G01B 9/02041* (2013.01); *G01B 9/02069* (2013.01); *G01B 9/02083* (2013.01); *A61B 5/0066* (2013.01); *A61B 2560/0223* (2013.01); *G01B 2290/60* (2013.01); *G01B 2290/65* (2013.01)

(58) Field of Classification Search
    CPC ............ G01B 2290/65; G01B 2290/60; A61B 5/7257; A61B 5/7203; A61B 3/10; A61B 2560/0223; A61B 5/0066
    See application file for complete search history.

(56) References Cited

U.S. PATENT DOCUMENTS

| | | | |
|---|---|---|---|
| 2017/0241763 A1* | 8/2017 | Wang | G01B 9/0207 |
| 2017/0248405 A9* | 8/2017 | Jiang | G01B 9/02027 |

FOREIGN PATENT DOCUMENTS

| | | |
|---|---|---|
| EP | 3211365 | 8/2017 |
| EP | 3239651 | 11/2017 |

OTHER PUBLICATIONS

Tsai et al. "Microvascular Imaging Using Swept-Source Optical Coherence Tomography with Single-Channel Acquisition," Applied Physics Express, 2011, vol. 4, Article 097001, 4 pages.

Decision to Grant with English Translation for German Patent Application No. 102018212100.1, dated Sep. 18, 2019, 23 pages.

Huber et al. "Amplified, frequency swept lasers for frequency domain reflectometry and OCT imaging: design and scaling principles," Optics Express, May 2005, vol. 13, No. 9, pp. 3513-3528.

International Search Report and Written Opinion for International (PCT) Patent Application No. PCT/EP2019/069473, dated Oct. 29, 2019, 10 pages.

English Translation of the International Search Report for International (PCT) Patent Application No. PCT/EP2019069473, dated Oct. 29, 2019, 2 pages.

* cited by examiner

METHOD FOR MONITORING TIME-DEPENDENT PROPERTIES OF LIGHT DURING SCANNING SWEPT-SOURCE OPTICAL COHERENCE TOMOGRAPHY

CROSS REFERENCE TO RELATED APPLICATIONS

This application is a national stage application under 35 U.S.C. 371 and claims the benefit of PCT Application No. PCT/EP2019/069473 having an international filing date of 19 Jul. 2019, which designated the United States, which PCT application claimed the benefit of German Patent Application No. 10 2018 212 100.1 filed 19 Jul. 2018, the disclosure of each of which are incorporated herein by reference.

FIELD

The invention relates to a method for monitoring time-dependent properties of light during optical coherence tomography (OCT) with a light source having a tunable wavelength, in particular with a periodically tuned laser light source ("swept source"), wherein a sample is illuminated in an illumination point on the surface of the sample and the illumination point is guided by an electronically actuatable deflecting device ("scanner") along a predetermined trajectory.

BACKGROUND

Optical coherence tomography is one of the most important optical microscope imaging techniques in medicine. Worldwide sales of OCT amount to more than one billion dollars per year. At present, most of the OCT systems use spectrometer-based measurement techniques—commonly known as Fourier-domain OCT (FD-OCT)—without lasers.

However, more and more OCT systems which employ a rapid wavelength-tunable laser have come into use recently. These are known as swept-source OCT (SS-OCT) units and offer many advantages: larger measurement areas can be detected and lower noise levels can be realized than with FD-OCT or even with time-domain OCT (TD-OCT), which work with broadband light sources and time-variable reference arm lengths. Furthermore, it is expected that only the rapid scanning SS-OCT will make it possible to sweep many millions of depth scans—or so-called A-scans—of a sample per second.

SUMMARY

Exactly one depth scan is swept when the laser is tuned once entirely over its wavelength range. Such a single tuning is also known as a "sweep" and the time span required by the laser to perform one sweep is known as the sweep duration.

In a scanning SS-OCT system, at least one A-scan is performed at each illumination point on the sample, with a scanner moving the illumination point over the sample (the "flying spot" layout). The shorter the sweep duration can be configured, the faster the illumination spot can be moved, among other things.

Further increasing of the OCT measurement speed requires an increasing of the wavelength tuning rate, or sweep rate, of the laser light source used. At present, the fastest tunable lasers used for OCT systems with the classic "flying spot" design are the so-called Fourier domain mode locked (FDML) lasers.

The scanning SS-OCT systems record the OCT measurement signal as a function of time. A photodiode measures the time-dependent signal that results from superimposing the light scattered back from the sample with a reference light component of the laser light. It thereby converts the time-dependent optical signal into a time-dependent electric signal. This signal is supplied to the input of an analog-digital converter (AD-converter or also ADC) and converted by this into a digital OCT signal for further processing—and possibly also for nonvolatile storage—in a digital signal processor (DSP), such as a PC or FPGA.

Further processing may involve, for example, a Fourier transformation, a multiplication by a variable amplitude (e.g., for "apodizing, spectral shaping"), or logarithmization. Another customary step prior to the Fourier transformation is recalibration—alternatively also known as remapping or resampling—in which the digitized measurement values are interpolated at intermediate reference points.

The digitized OCT signal in an ideal measurement layout would be influenced only by the scattering properties or structures in the sample—in many cases a biological tissue. The time-dependent OCT signal is correlated with the time-dependent position of the illumination point moved over the sample and thus receives its location assignment. By putting together a plurality of A-scans registered along the scan trajectory, cross-sectional images of the sample can be reconstructed in the computer (B-scans), and volume representations (C-scans) can be determined by putting together such cross-sectional images for adjacent trajectories. This is the principle, among other things, behind medical imaging by means of SS-OCT.

In real-world measurement apparatuses, a wide variety of error sources may play a role, which it is possible and desirable to cancel out mathematically in the digitized OCT signals. Perhaps the most important error source is the tunable laser light itself. The light supplied to the OCT interferometer may exhibit both intensity and phase fluctuations, and the wavelength tuning may also have an inter-sweep variability.

In the case of tunable-wavelength lasers, one tries to ensure that the wavelength $\lambda(t)$ preferably changes linearly over time, i.e., within one sweep the wavelength $\lambda$ varies uniformly in equal time steps $\Delta t$ by the same constant increment $\Delta\lambda$. In the case of very fast tunable lasers, such as FDML lasers, this is usually no longer possible, for example on account of mechanical resonances of the optical tuning filter. For the optical frequency $\omega=ck=2\pi c/\lambda$ (where c is the speed of light), the linear variation over time is generally not achieved by the tuning of the laser, yet it is still desirable for the digitized OCT signal to be a function of the optical frequency at equidistant reference points for further OCT evaluation using fast and efficient FFT algorithms.

AD-converters can generally be actuated with clock signals if one wishes to digitize analog measurement values on predetermined, non-equidistant time reference points. In the case of SS-OCT, this is also known as "k-clocking", in order to detect the electric OCT signal directly in the optical frequency in an equidistant manner. However, k-clocking is practically impossible for high-speed AD-converters, which are supposed to process signals with frequency components significantly larger than 1 GHz. The architecture of such ADC units is designed to be operated with a particular stable sampling rate. Both aperiodic jumps (jitter) and periodic phase shifts of the sampling signal result in substantial falsifications of the digitized signal.

If one wishes or is required to forego k-clocking, in its place one must then detect at least one additional monitor signal representing the optical properties of the light being furnished to the OCT interferometer.

The at least one monitor signal is thereby produced as an optical signal, namely, a time-dependent light intensity, and it is converted by a photodetector into a time-dependent electric monitor signal. As such, it is then either taken to a second input of the (primary) AD-converter or to a separate, synchronous, rigid phase clocked (auxiliary) AD-converter and digitized simultaneously with the electric OCT signal. The at least one optical monitor signal may be generated for example in a monitor device, which is supplied with a portion of the laser light so as to interfere with itself in a predetermined manner. The corresponding digitized monitor signal then allows an inference to be made regarding the wave number position of the laser at the points in time when the digitized OCT signal is also present, cf. R. Huber, M. Wojtkowski, K. Taira, J. G. Fujimoto, and K. Hsu, "Amplified, frequency swept lasers for frequency domain reflectometry and OCT imaging: design and scaling principles," Optics Express 13, 3513-3528 (2005).

The problem serving as a basis for the present invention is that each usable or even required monitor signal may have frequencies comparable to the OCT signal. If one uses an AD-converter already for the processing of the electric OCT signal in the threshold range of its processing speed, a monitor signal could only then be digitized using a separate, relatively powerful AD-converter. And high-speed AD-converters are by far the most costly electronic components of a rapid scanning SS-OCT system. Moreover, an effective reduction of the very extensive data stream produced during OCT by a factor of ~2 would be helpful in achieving more high-performance OCT systems. But with each new ADC generation, one will surely reach the limits again of the then achievable data stream transmission rates.

The object of the invention is to propose an improved monitoring the time-dependent properties of light during OCT.

The problem is solved by a method for monitoring time-dependent properties of light during scanning swept-source optical coherence tomography, having the steps:
 a. generating laser light having wavelengths that change on a time-dependent basis and a predetermined sweep duration;
 b. splitting the laser light into sample light, reference light, and monitor light;
 c. routing the reference light into a reference arm of an OCT interferometer;
 d. routing the monitor light into a monitor device, which generates at least one optical monitor signal representing at least one time-dependent property of the monitor light;
 e. generating at least one electric monitor signal from the at least one optical monitor signal with a light detector;
 f. illuminating in a point-shaped manner a sample with sample light, wherein the illumination point is guided on the surface of the sample along a predetermined trajectory;
 g. superimposing the light scattered by the sample with the reference light emerging from the reference arm on a light detector to generate an electric OCT signal; characterized in that
 h. the at least one electric monitor signal and the electric OCT signal are AD-converted in alternating sequence, in each case equidistantly in time, by means of which a single digital data stream comprising time segments each having only one of the AD-converted signals is formed.

The dependent claims indicate advantageous embodiments of the method.

The method according to the invention has the immediately obvious advantage that only a single high-performance AD-converter or AD-converter channel is required to digitize the at least one monitor signal and the OCT signal, although now no longer entirely, but only in respective time segments provided for this. This may mean rejecting the OCT signal on a time segment basis, but this need not mean a loss, as shall be explained further below.

The invention is based, among other things, on the very surprising observation and discovery that both intensity and phase noise of many SS-OCT light sources exhibit a certain correlation. Thus, the noise after some tens to hundreds of wavelength passes does not behave in an entirely erratic manner, but instead shows certain correlations. Hence, a recalibration, a renormalization, or even only a recording of the reference signal need not be done absolutely at each individual measurement point.

It should be noted that the invention can be realized preferably with a Fourier domain mode-locked (FDML) laser as the OCT light source.

The points in time at which the signals alternate during the digitization according to the invention must be known. These points in time are generally relatively easy to find from the time-indexed data stream from the AD-converter, i.e., the continuous digital value table of the electric signals, since the at least one monitor signal is unaffected by the sample and therefore can be easily distinguished from the OCT signal. Alternatively, however, additional synthetic "blips" (short peaks or valleys in the signal of the light detector) can be added to the signals when a signal change occurs in the data stream. Such blips may also contain additional information, such as indexing.

When a plurality of monitor signals is to be digitized in an alternating sequence according to the invention, it may be helpful either to log the points in time of the change between two monitor signals or to frame each time segment with one of the monitor signals of two time segments with the OCT signal. In the latter case, the points in time of the change are again easily found in the data stream. Such repeatedly recorded different monitor signals may be helpful, e.g., when the analytical signal of the wavelength beat signal is to be measured directly by using a 3×3 coupler.

When the alternation of the signals is controlled actively, the points in time are then known exactly. This is the usual operating mode of the invention. It is thereby advantageous, but in no way necessary, to induce the alternating of the signals during the AD-conversion in a periodic manner.

Alternating the signals can be achieved, for example, by activating a switch, which routes one of at least two input signals onto a signal path ultimately leading to an AD-conversion. Activating the switch may thereby occur by a switch actuation, which is also designed to communicate at least one switch signal to the AD-converter at the instant of the activation. The AD-converter can then mark or log the switching process in the generated data stream. Activating the switch can occur in a periodic manner; in this case, the switch may also switch autonomously at a fixed predetermined frequency. The fixed frequency simplifies finding the switching processes in the data stream even when the AD-converter receives no marking signals.

The method according to the invention can be used in theory for SS-OCT systems with any given sweep and scan rate. It may be used in a particularly advantageous manner when the at least one monitor signal and the OCT signal have frequency components above 400 MHz and are AD-converted with a high-speed AD-converter, having a sampling rate of 800 Msamples/s or more.

For example, and preferably, the electric OCT signal and the at least one electric monitor signal may be generated with the same light detector, wherein the at least one optical monitor signal and the sample and reference light are routed to the light detector in alternating sequence by repeated activation of an optical switch. For clarification purposes, this means that sample and reference light are jointly supplied to one of the inputs of the optical switch. Consequently, in one position of the switch this sample and reference light jointly reach the light detector to generate the OCT signal, while in a second position of the switch only monitor light is conducted to the light detector.

In an alternative and particularly preferred embodiment, the electric OCT signal is generated with a first light detector and the at least one electric monitor signal is generated with at least one second light detector, wherein the electric signals are routed to the same input of the AD-converter in alternating sequence by repeated activation of an electric switch. This embodiment needs a fast switch—i.e., one that can be switched within one sweep period. Among other things, commercially available standard assemblies—RF switches—are suitable for this.

Despite the additional light detector needed, the use of an additional electric signal path should generally be more economical than a comparable optical switch.

The switching of the electric signal path can also be realized with a purely digital switch by selecting a fast AD-converter which can choose between multiple input signals and be reconfigured dynamically between converting the main signal and the monitor signal. This configuration can be achieved both by an electric control signal and by a logical configuration using a digital control register. The latter requires the contents of a control register to be loaded in very short time. For typical high-speed AD-converter ICs, the usual loading times for a control register are on the order of 100 nanoseconds, or even less if the control registers are double-buffered, and are only updated by a synchronization or selection signal. The new configuration is then usually adopted in less than 10 microseconds. Hence, for B-scan rates in the kHz range and for typical C-scan depths of around 500 B-scans, there are still at least 10 time segments with digitized monitor signals for each OCT C-scan.

The invention proposes that all of the aforementioned electric signals—in any given alternating sequence—are digitized by the ADC with a predetermined sampling rate, which is chosen optimally for the architecture of the ADC. Accordingly, the signals are AD-converted equidistantly in time, and no k-clocking occurs.

BRIEF DESCRIPTION OF THE FIGURES

The invention is also explained below with the aid of figures. There are shown.

DETAILED DESCRIPTION

Figure 1:
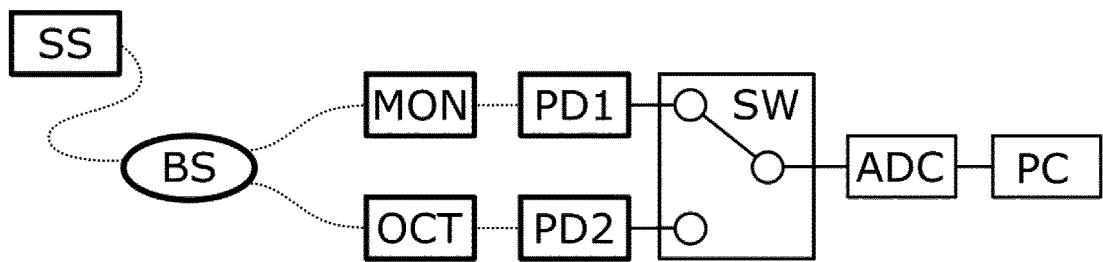
FIG. 1 a sketch of a measurement setup implementing the invention.

FIG. 1 shows the schematic setup of a SS-OCT system in which the method according to the invention is used. The light of a swept-source laser light source (SS) is supplied to a beam splitter (BS) and split there into monitor light, sample light, and reference light. The monitor light is routed to a monitor device (MON), and the sample and reference light to an OCT system (OCT) comprising an interferometer. It should be noted that the light of the laser is usually conveyed in fibers, and that it is advisable to supply the sample and reference light in a common fiber to the OCT. The actual splitting then occurs by a second beam splitter or fiber coupler in the OCT system.

Merely to simplify the description, it is assumed that precisely one optical monitor signal is obtained from the monitor light in this case.

FIG. 1 shows the embodiment in which the optical monitor signal generated and the optical OCT signal generated by superimposing sample and reference light are each converted into electric signals by their own respective light detector (PD1, PD2). The outputs of the light detectors are connected to the inputs (two, in this case) of an electric switch (SW), which selectively forwards the one or the other electric signal to its single output. The position of the switch determines which of the electric signals will be present at the output and be digitized by the downstream AD-converter (ADC). The data stream at the output of the ADC is supplied to a digital signal processor, such as an ordinary PC, wherein the signal processing chain processes the raw signal into images (and—depending on the application—additional information levels) and stores them if necessary. The electric switch SW receives control signals determining its switching condition. The source of the control signals may be a clock, which initiates a chronologically periodic switching between states. A human user himself will not generally trigger the changing of the switching states, but rather select and specify the clock frequencies. The clock may also be phase-locked with other oscillators and thus be synchronized with frequencies other than the preset ones.

Figure 2:
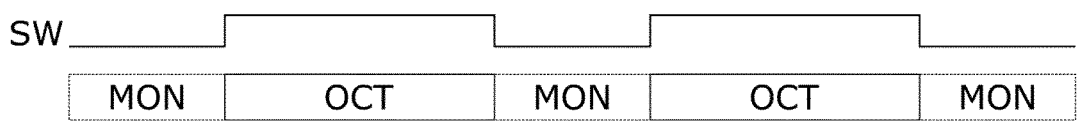
FIG. 2 a visualization of the structure of the generated data stream.

Quite generally, the sketch of FIG. 2 shows a time axis running from left to right, wherein in the upper region a periodic control signal for the switch (SW) is represented by a square wave. The band in the lower region illustrates the time-indexed data stream emerging from the AD-converter. It comprises separate, contiguous time intervals in which either only the digitized monitor signal (MON) or the digitized OCT signal (OCT) appear in the data stream. The lengths of the time intervals in FIG. 2 are chosen arbitrarily for purposes of illustration. They may differ significantly for the MON and the OCT signal.

As already mentioned, a predetermined portion of the OCT signal is not detected when implementing the invention, i.e., it is rejected. However, this does not mean any actual loss of information.

Figure 3:
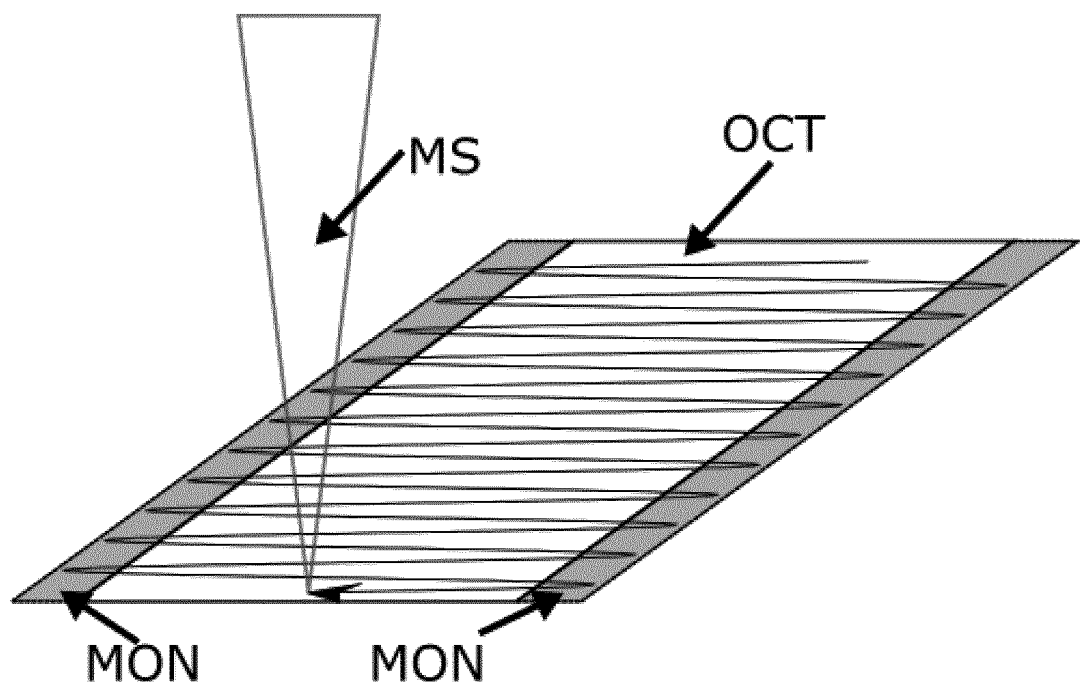
FIG. 3 a sketch for selecting switching points in time.

For example, FIG. 3 shows a situation in which the laser beam (MS) is focused into an illumination point which is routed by means of a deflecting device along a roughly sinusoidal trajectory (OCT) on a sample surface. At the reversal points there is necessarily a decrease in the path velocity of the illumination point (due to a reversal of direction), and in this region the applied radiation dose increases accordingly. For that reason, when sensitive tissue samples are involved, consideration is given to interrupting the laser beam during the time of the beam reversal or at least to fade it out from the beam path to the sample. Thus, no OCT measurement data is available any way for time slots when the illumination point is in one of the dark bands (MON) in FIG. 3. Precisely in these time slots, the monitor signal can be detected without further impairing the OCT measurement.

It is therefore a preferred embodiment of the invention for the illumination point on the sample to be routed by an actuatable deflecting device, wherein the actuation of the deflecting device communicates with the electric or optical or digital switch for alternating the signals and instructing the switch to supply at least one monitor signal to the AD-converter during those time segments when the illumination point passes through reversal points of the trajectory. In this case, therefore, the actuator of the scanner is either simultaneously itself a clock of the switch SW in FIG. 1 or is phase-locked to the clock. The scanner and the actuator are also comprised in the OCT system in FIG. 1.

Measurement setups in which the illumination point travels on trajectories having only a very few or no reversal points, such as a rotating, sideways pointing scanner in an OCT endoscope or the like, may also profit from the invention if the laser light source has short sweep durations, and the illumination point is moved quickly over the sample.

It is greatly advantageous here for the sweep duration to be configured for less than 3 microseconds, which is possible today with the FDML lasers mentioned at the beginning. Furthermore, the FDML lasers prove to be very stable in terms of their wavelength tuning characteristic, which in turn is to be determined for the recalibration during an OCT measurement repeatedly, [or] ideally in a periodically recurring basis, using one monitor signal. One only needs to measure a single sweep with the monitor device to robustly infer many hundreds of subsequent sweeps.

In order not to sacrifice more than one OCT measurement point for detecting the monitor signal, it is advantageous for the length of a time segment in which the data stream contains only the at least one monitor signal to be greater than the sweep duration and smaller than the time in which the illumination point is moved on the surface of the sample along the trajectory about an illumination point diameter. Assuming that the monitor signal detected in this way preserves its informative value for a large number of subsequent sweeps, this is applicable even for large sweep durations and appropriately low scanning speeds. With FDML lasers as swept-source light sources, this precondition is fulfilled in any case, and it is advantageous when the length of a time segment in which the data stream comprises only the OCT signal is greater than 100 times the sweep duration, preferably even greater than 500 times the sweep duration. In this way, it is ensured that the user may lose at most one percent of the theoretically available OCT image information, usually even much less.

On the other hand, the costs of the OCT system are significantly reduced by omitting the second AD-converter—even almost by half in the case of a high-performance ADC for very rapid systems. Moreover, it now becomes possible to register monitor signals by using many common optical or electronic components. This has the advantage that the disruptive effects due to any different signal transit times are suppressed to the greatest extent possible.

The reduction of the data stream and the associated cost savings are even greater by measuring not just one monitor signal, but for example two 120° phase-shifted signals and an intensity trend. In this way, one already has a reduction by a factor of four. With a plurality of monitor signals, one can fully detect the complete wavelength pass of the laser with intensity and phase down to a fixed factor. This allows a maximum level of precision during recalibration.

For the more stable, precise or robust generating of a monitor signal for recalibration purposes, it may be helpful to record a plurality of self-interfering signals of the monitor light, obtained from a plurality of interferometers each with different optical arm length differences, as the monitor signal. This allows one to achieve a good recalibration both in small and large OCT scan depths. For example, the different optical monitor signals can be electronically detected simultaneously and be routed according to the invention during a time slot in which only the at least one monitor signal is to be detected (cf. FIG. 2 MON), in alternating time sequence, as electric monitor signals to the same input of the ADC, i.e., only a single data stream is also formed in this case from the different monitor signals.

Besides the cost reduction, a primary consideration is that for the first time extremely fast OCT systems are made possible by the invention. Because an absolute limit exists in the bus systems of the computer hardware used, it is not possible to increase the data stream rate efficiently, even at the cost of major financial outlay. Since the optical systems of the SS-OCT devices today generate much larger information streams than can be processed as data, the trend will continue of being always limited by a "bottleneck" of the bus system in the computer system. This limitation is likewise at least mitigated by the invention described herein, i.e., the bottleneck is broadened out, and the limit of what is feasible is moved upward.

What is claimed is:

1. A method for monitoring time-dependent properties of light during scanning swept-source optical coherence tomography (OCT), the method comprising:

generating laser light having wavelengths that change on a time-dependent basis over a predetermined sweep duration;

splitting the laser light into sample light, reference light, and monitor light;

routing the reference light into a reference arm of an OCT interferometer;

routing the monitor light into a monitor device, which generates at least one optical monitor signal representing at least one time-dependent property of the monitor light;

generating at least one electric monitor signal from the at least one optical monitor signal;

illuminating in a point-shaped manner a sample with the sample light, wherein an illumination point of the sample light is guided on the surface of the sample along a predetermined trajectory;

superimposing light scattered by the sample with the reference light emerging from the reference arm to generate an electric OCT signal;

wherein the at least one electric monitor signal and the electric OCT signal are routed to an AD converter using an electronic switch, and are AD-converted in alternating sequence, in each case equidistantly in time, to form a single digital data stream comprising time segments each having only one of the AD-converted signals, wherein a set of sweeps from which the at least one electric monitor signal is derived is smaller than a set of sweeps from which the electric OCT signal is derived.

2. The method according to claim 1, wherein the at least one electric monitor signal and the electric OCT signal have frequency components above 400 MHz and are AD-converted using a high-speed AD-converter.

3. The method according to claim 1, wherein the electric OCT signal is generated using a first light detector and the at least one electric monitor signal is generated using at least one second light detector, wherein the electric OCT signal and the at least one electric monitor signal are routed to a same input of the AD-converter in alternating sequence by repeated activation of the electronic switch.

4. The method according to claim 3, wherein the illumination point on the sample is guided by an actuatable deflecting device, wherein an actuator of the deflecting device communicates with the optical switch for alternating the at least one optical monitor signal and the sample and reference light and for instructing the optical switch to supply the at least one electric monitor signal to the AD-converter during such time segments in which the illumination point passes through reversal points of the predetermined trajectory.

5. The method according to claim 1, wherein the electric OCT signal and the at least one electric monitor signal are generated using a same light detector, wherein the at least one optical monitor signal and the sample and reference light are routed to the same light detector in alternating sequence by repeated activation of an optical switch.

6. The method according to claim 1, wherein the sweep duration is less than 3 microseconds.

7. The method according to claim 6, wherein a length of a time segment in which the digital data stream is based on only the electric OCT signal is greater than 100 times the sweep duration.

8. The method according to claim 1, wherein a length of a time segment in which the digital data stream is based on only the at least one electric monitor signal is greater than the sweep duration and smaller than a time segment in which the illumination point is moved on the surface of the sample along the predetermined trajectory about an illumination point diameter.

9. The method according to claim 1, wherein a plurality of electric monitor signals are routed in alternating sequence to a same input of the AD-converter.

10. The method according to claim 9, wherein a wavelength pass of the laser light is derived from the plurality of monitor signals.

* * * * *